United States Patent [19]

Mitsuhashi et al.

[11] Patent Number: 4,501,736

[45] Date of Patent: Feb. 26, 1985

[54] EXTRACT FROM BARRENWORT

[75] Inventors: Susumu Mitsuhashi, Musashino; Muneaki Takase, Oizumi; Sosuke Yasui, Tokyo; Ichiro Washizawa, Maebashi; Kimitomo Yoshioka, Tokyo, all of Japan

[73] Assignee: Zenyaku Kogyo Kabushiki Kaisha, Tokyo, Japan

[21] Appl. No.: 520,760

[22] Filed: Aug. 8, 1983

Related U.S. Application Data

[63] Continuation of Ser. No. 258,390, Apr. 28, 1981, abandoned.

[30] Foreign Application Priority Data

Apr. 30, 1980 [JP] Japan .................................. 55-57424
Jun. 20, 1980 [JP] Japan .................................. 55-83539

[51] Int. Cl.³ ............................................. A61K 35/78
[52] U.S. Cl. .................................................... 424/195
[58] Field of Search ........................................ 424/195

[56] References Cited

PUBLICATIONS

Derwent, Abst. No. 80460, D/44, 1980.

*Primary Examiner*—Albert T. Meyers
*Assistant Examiner*—John W. Rollins, Jr.
*Attorney, Agent, or Firm*—Scrivener, Clarke, Scrivener and Johnson

[57] ABSTRACT

The present invention provides an extract obtained by extracting a plant belonging to the genus Epimedium sp. with a mixed solvent of water and a water-miscible organic solvent or with water, defatting the obtained aqueous extract and collecting a high-molecular compounds-containing fraction from the defatted aqueous extract, a process for preparation of this extract, an antibacterial agent comprising this extract as an effective component and an antibacterial therapy by using this extract.

9 Claims, 2 Drawing Figures

EXTRACT FROM BARRENWORT

This application is a continuation of application Ser. No. 258,390, filed Apr. 28, 1981, now abandoned.

BACKGROUND OF THE INVENTION

The present invention relates to an extract obtained from the herb of plants belonging to the genus Epimedium sp. of the family Berberidaceae, a process for preparation of this extract, an antibacterial agent comprising this extract as an effective component, and an antibacterial therapy by using this extract.

As the plant belonging to the genus Epimedium sp., there are known *Epimedium macranthum*, M. et. D, var, violaceum, Fr., *Epimedium sagittatum*, Bak., *Epimedium macranthum*, M. et. D., *Epimedium koreanum*, Nak., etc. These plants are perennial herbs growing naturally in Japan, China and Korea, etc. The stalks, leaves and roots are called "Inyokaku" in the field of Chinese medicines. The herb of such plant is infused and used as a cordial or tonic medicine. The effect is not substantially different among species of plants belonging to the genus Epimedium sp. A single species or a mixture of two or more of species is marketed as a crude drug called "Barrenwort". Components of this Barrenwort have been studied from old and reports have been published, for example, by: Akai et al., Yakugaku Zasshi, 55, 537, 705, 719, 788 and 1139 (1935); Tomita et al., Yakugaku Zasshi, 77, 114 and 212 (1957), Maeda, Tohio Izi Sinsi, No. 2133 and 2795 (1932); Miyake, Okayama Igakkai Zasshi, 49, (10) and 2043 (1937); and Hirashima et al., Clinical Report, 4, 139 (1970). But their details are still unclear in many points.

We have conducted research on this Barrenwort and found that an extract obtained by extracting plants belonging to the genus Epimedium sp. with a mixed solvent of water and a water-miscible organic solvent or with water and collecting a high-molecular compounds-containing fraction from the obtained aqueous extract has an excellent antibacterial activity. We have now completed the present invention based on this finding.

DETAILED DESCRIPTION OF THE INVENTION

Figure 1:
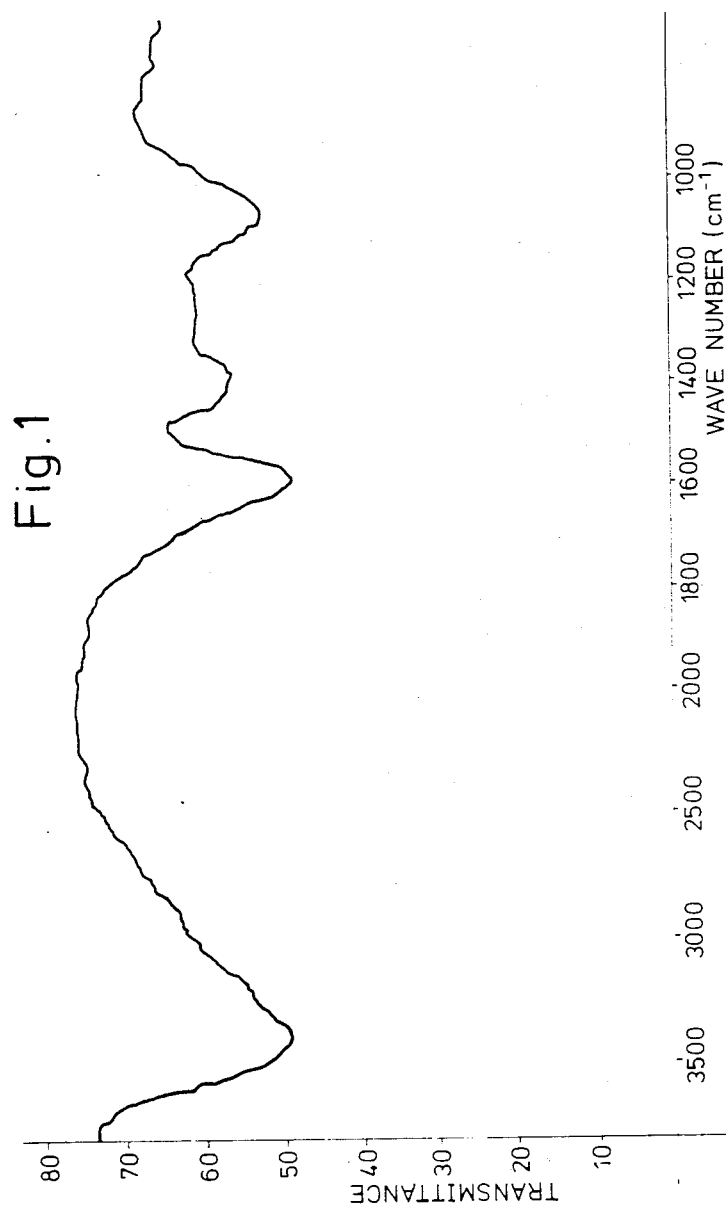

The present invention will now be described in detail.

A plant belonging to the genus Epimedium sp. is extracted with a mixed solvent of water and a water-miscible organic solvent or with water, and the obtained extract is concentrated under reduced pressure. As the water-miscible organic solvent there can be used, for example, lower alcohols such as methanol, ethanol and isopropanol, ketones such as acetone and water-miscible ethers such as dioxane and the like. A mixture of two or more of these water-miscible solvents may also be used. Furthermore, lower aliphatic acids such as acetic acid having a concentration lower than 1 normality, water-miscible lower amines such as ethanolamine at a concentration lower than 1 mol/l and alkaline hydroxides easily soluble in water such as sodium hydroxide having a concentration lower than 1 normality can be used as the extraction solvent.

With regard to the mixing ratio of water and the organic solvent, it is preferred that the amount of the organic solvent be smaller than 50% by volume. In view of the concentration operation, it is preferred that the operation of obtaining the intended aqueous extract be carried out by using a mixed solvent of a water-miscible organic solvent and water.

In the present invention, commercially available herb of Barrenwort may be used as it is, but it is preferred that it be used after it has been finely divided into pieces.

One embodiment of the extraction operation will now be described.

Barrenwort is allowed to stand in the above-mentioned extraction solvent at room temperature for several to several tens of hours, and filtration is then carried out to obtain a filtrate. The residue is subjected to extraction and filtration in the same manner, and these operations are repeated. All the obtained filtrates are combined and concentrated under reduced pressure to obtain an aqueous extract. The extraction is usually effected at room temperature, but may be effected while heating in order to shorten the extraction time. This extraction with heating is preferably carried out on a water bath at a water bath temperature of 35° to 55° C. for 4 to 6 hours using a reflux condenser. It may be effected according to the percolation method. The amount of the solvent used is 5 to 15 times (V/W) that of the plant belonging to the genus Epimedium sp. The extraction residue is preferably subjected to extraction under the same conditions 3 or more times using the solvent in an amount 0.4 to 0.6 times (V/V) that of the solvent first used. The separation may be accomplished by paper filtration or centrifugalization or the like, but better results are obtained when suction filtration is carried out by using commercially available filter aids for example Radiolite (supplied by Showa Chemical Industry Co., Ltd., Japan), Celite (supplied by Wako Junyaku Industry Co., Ltd., Japan) or Fibra Cel (supplied by Johns Manville Co., Ltd., U.S.A.), etc. The reduction of the pressure is accomplished by conventional manners for example an aspirator or a vacuum pump or the like. An extraction vessel having the inner surface lined with glass or covered with enamel or an extraction vessel made of stainless steel is used.

The so obtained aqueous extract is then defatted. The defatting operation is ordinarily accomplished by adding one or more organic solvent selected from lower aliphatic esters such as ethyl acetate, halogenated hydrocarbons such as chloroform, water-immiscible ethers such as diethyl ether and aliphatic hydrocarbons such as n-hexane and the like, sufficiently shaking the mixture and collecting the aqueous layer alone. The obtained aqueous layer is subjected to the same operation again and is heated on a water bath to remove the organic solvent left in a small amount, and then filtered to obtain a defatted aqueous extract. It is preferred that the solvent be used in an amount 0.5 to 1.5 times (V/V) that of the aqueous extract for each operation and the operation be repeated 3 to 5 times. There may be adopted a method in which the defatting operation is first conducted and the extraction operation with a mixed solvent of a water-miscible organic solvent and water or with water is then carried out.

Then, a high-molecular compounds-containing fraction is collected from the defatted aqueous extract by fractional precipitation, dialysis or other conventional manners. These known manners may be used in combination for collection of the high-molecular compounds-containing fraction. The collected fraction is concentrated under reduced pressure to obtain the intended extract.

This operation will now be described in detail with reference to the following two specific embodiments.

(1) A water-miscible organic solvent is added to the defatted aqueous extract at room temperature to effect the precipitation. The amount of the solvent used is not smaller than that of the aqueous extract (V/V). The deposited precipitate is recovered by filtration and is washed with a water-miscible organic solvent in an amount 5 to 20 times (V/W) that of the precipitate. The washed precipitate is poured into water in an amount 20 to 50 times (V/W) that of the precipitate. Then, a water-miscible organic solvent is added to the solution in an amount 3 or more times (V/V) that of the solution to effect precipitation again. The formed precipitate is recovered by filtration and dried under reduced pressure to obtain the intended extract. As the water-miscible organic solvent, there may be used, for example, lower alcohols such as methanol and ethanol and ketones such as acetone and the like. A mixture of two or more of these organic solvents may also be used. The so obtained extract may be purified by extraction with water. More specifically, the extract is mixed with water in an amount 20 or more times (V/W) that of the extract at room temperature, and the mixture is sufficiently stirred and is then filtered. The filtrate is concentrated to dryness under reduced pressure to obtain a purified extract. At this operation, separation of the precipitate from the filtrate is accomplished by paper filtration or by centrifugalization.

(2) The defatted aqueous extract is charged in a semipermeable membrane such as a cellulose tube for dialysis, and dialysis is carried out by using distilled water or city service water as the external liquid and the internal liquid (the portion which includes high-molecular compounds-containing fraction) is collected. Better results are obtained when the external liquid is stirred by a stirrer or is kept running. It is preferred that the dialysis be conducted for about 1 week if the operation is carried out while keeping the external liquid running. In addition to this dialysis method, there may be adopted the gel filtration, the ultrafiltration, the ultracentrifugalization and the reverse osmosis. Two or more of these methods may be adopted in combination. From the industrial viewpoint, it is preferred that the dialysis operation be carried out by using a dialysis apparatus including a hollow fiber membrane, for example PVA Hollow Fiber Dialyzer (supplied by Kuraray Co., Ltd., Japan), SF Filtration System (supplied by Kuraray Co., Ltd., Japan) or Nitto Module (supplied by Nitto Denko Co., Ltd., Japan) or the like.

The salting-out operation may be conducted as the preliminary treatment before the dialysis operation. More specifically, a known water-soluble salt is added to the defatted aqueous extract to a saturation concentration, and the deposited precipitate is recovered and dissolved in water and the dialysis operation is then carried out. As the salt to be used for the salting-out operation, there may be used, for example, chlorides such as sodium chloride, calcium chloride and aluminum chloride, nitrates such as potassium nitrate, calcium nitrate and aluminum nitrate, and sulfates such as ammonium sulfate and magnesium sulfate and the like.

The so obtained internal liquid (the portion which includes high-molecular compounds-containing fraction) is concentrated to about 1/10. A water-miscible organic solvent is added to the concentrated liquid in an amount 3 or more times (V/V) that of the concentrated liquid. The deposited precipitate is recovered by filtration and dried under reduced pressure to obtain the intended extract. As in the case of the embodiment (1) above, the so obtained extract may be purified by extraction with water.

Figure 2:
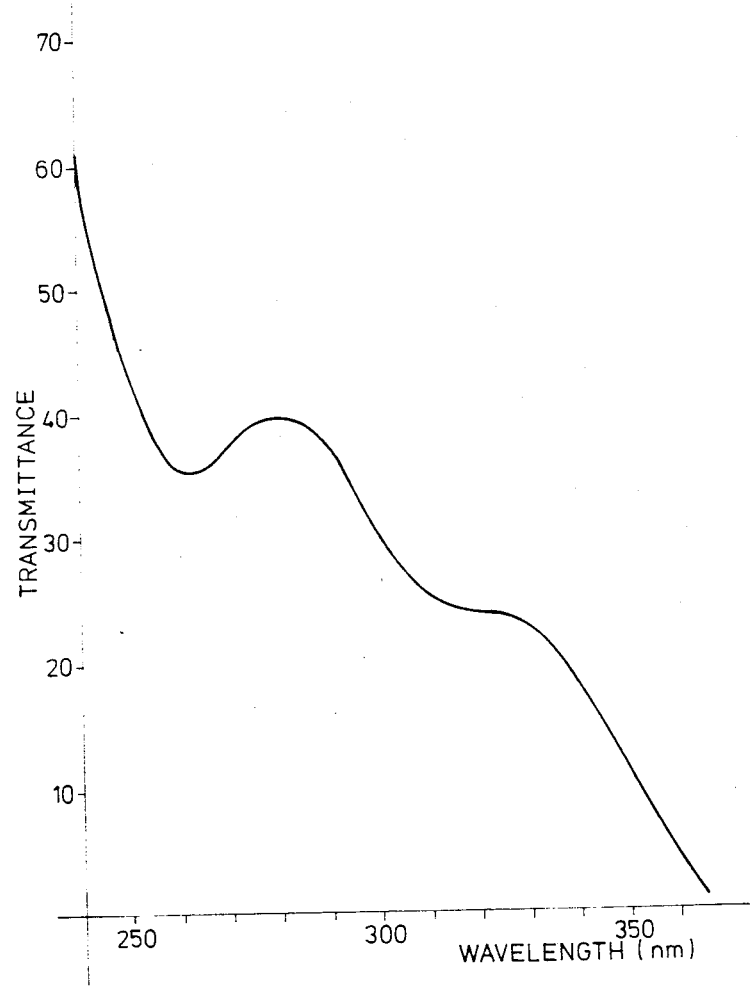

The so obtained extract according to the present invention has the following characteristics.
(1) Properties:
  (a) Brown powder
  (b) Weakly-acidic (pH of about 6.5) (when 100 mg of the extract is dissolved in 50 ml of water)
(2) Solubility:
  (a) Soluble in water
  (b) Insoluble in methanol, ethanol, acetone, ethyl acetate, diethyl ether, hexane and chloroform
(3) Color Reactions:
  Positive to (a) anthrone-sulfuric acid reaction, (b) Bial's reaction, (c) Molisch's reaction and (d) skatol reaction but negative to (a) ninhydrin reaction, (b) 2,4-DNP reaction, (c) Seliwanoff's reaction and (d) naphthoresorcinol reaction
(4) Saccharides composition:
  When 20 mg of the extract is hydrolyzed by adding sulfuric acid (1-N $H_2SO_4$, 5 ml) to the solution to make the normality of the solution unity, heated for 2 hours at 100° C., then neutralized by adding barium hydroxide to the solution, and subjected to paper chromatographic analysis, arabinose and galactose are detected.
(5) Infrared Absorption:
  Infrared absorption spectrum is shown in FIG. 1.
  $\nu_{max}^{KBr}(cm^{-1})$ 3400, 1600, 1400, 1100
(6) Ultraviolet Absorption:
  Ultraviolet absorption spectrum is shown in FIG. 2.
  $\lambda_{max}^{H_2O}(nm)$ 280, 325

In order to confirm the utility of the extract of the present invention, the following tests were carried out.
(1) Macrophage Phagocytic Function Test:
  ① Phagocytosis on *Staphylococcus aureus*:
  As the experimental animal, 7- to 10-weeks-old female mice of the ICR/JCL strain (having a body weight of 27±3 g) were used. After passage of 2 days from treatment of the sample, the intraperitoneal injection of the mice of the sample-treated group and the mice of the control group [treated with phosphate buffered physiological saline solution having a pH value of 7.0 (hereinafter referred to as "PBS")] were washed with RPMI-1640 medium [G. E. Moore, The Journal of the American Medical Association, 199, pages 519–524 (1967)] (supplied by Nissui Seiyaku Co., Ltd., Japan) to collect peritoneal exhaust cells (hereinafter referred to as "PEC"), and the collected cells were pooled respectively. The PEC were washed one time with RPMI-1640 medium, and then suspended in 10% FBS-RPMI-1640 medium (culture medium formed by adding 10% of Fetal bovine serum to RPMI-1640 medium). The cell suspension was adjusted to $1 \times 10^6$ cells per ml by using Türk solution. Then 2 ml of the so obtained PEC suspension was charged in a TD-15 bottle having 4 cover glass sheets attached thereto and culturing was conducted at 37° C. for 60 minutes in a 5% $CO_2$ incubator, and 0.1 ml of a suspension of Staphylococcus aureus 209P having a concentration of $4 \times 10^8$ cells per ml was added and culturing was further conducted for 20 minutes to effect phagocytosis. After culturing, the culture liquid was washed 3 times with Hanks' solution [J. H. Hanks and R. E. Wallace, Proceedings of the Society for Experimental Biology and Medicine, 71, page 196 (1949)] (supplied by Nissui Seiyaku Co., Ltd., Japan). The macrophage-adhering cover glass sheets were fixed by methanol and subjected to Giemsa staining to obtain samples for counting the number of phagocytized bacteria and 200 macrophages were counted in each cover glass sheet microscopical observation with oil immersion objective (1000 to 2000 magnifications) to determine the phagocytosis ratio and mean phagocytized bacteria number (phagocytized bacteria number I). Furthermore, the number of bacteria phagocytized by 100 phagocytizing macrophages was counted to determine the mean phagocytized bacteria number (phagocytized bacteria number II).

Phagocytosis ratio =

$$\frac{\text{number of phagocytizing macrophages}}{200 \text{ (macrophages)}} \times 100 \text{ (\%)}$$

Phagocytized bacteria number I =

$$\frac{\text{number of phagocytized bacteria}}{200 \text{ (macrophages)}}$$

Phagocytized bacteria number II =

$$\frac{\text{number of phagocytized bacteria}}{100 \text{ (phagocytizing macrophages)}}$$

Activation index = $\frac{\text{each measured value } (\overline{M}) \text{ of treated group}}{\text{each measured value } (\overline{M}) \text{ of non-treated group}}$ The obtained results are shown in Table 1.

(2) Phagocytosis Test on *Salmonella Enteritidis*:

The test was carried out in the same manner as described in (1) above except that *Salmonella enteritidis* 116–45 was used as the test bacteria and culturing was conducted for 60 minutes after addition of the bacteria suspension. Calculation was conducted in the same manner as described in (1) above. The obtained results are shown in Table 1.

ner Co., Ltd., West Germany) was injected into tail veins of the respective mice of the treated group and control group after passage of 24 hours from the last treatment, and the clearance from blood was examined according to the following procedures. More specifically, colloidal carbon was diluted with a physiological saline solution containing 3% of gelatin so that the carbon concentration was reduced to ½ and the dilution was injected into the tail vein at a rate of 10 ml/kg. Then, 0.010 ml of blood was collected by a heparin-treated microppipette according to the eyepit puncture method and immediately transferred into 2 ml of 0.1% $Na_2CO_3$ to dissolve the blood. The absorption at 650 nm was measured by Hitach Double Beam Model 124 (supplied by Hitachi Co., Ltd., Japan). The phagocytic index was determined by injecting the colloidal carbon dilution into the vein, collecting blood after passage of 2 minutes ($t_1$) and 20 minutes ($t_2$) and performing calculation based on the carbon concentrations ($C_1$ and $C_2$: after passage of 2 minutes and 20 minutes, respectively) in samples bloods according to the following formulae:

Phagocytic index: $K_2^{20} = \frac{(\log C_1) - (\log C_2)}{t_2 - t_1}$

Half-life period in blood: $T\frac{1}{2} = \frac{0.301}{K_2^{20}}$

The obtained results are shown in Table 2.

TABLE 2

| | | Results of Reticuloendothelial Function Test | |
|---|---|---|---|
| | | $K_2^{20}$ | T ½ (min.) |
| Test 1 | Control mice | 0.0137 ± 0.0039 | 23.945 ± 7.793 |

TABLE 1

| | | Results of Macrophage Phagocytosis Test | | | | |
|---|---|---|---|---|---|---|
| | | | (1) *Staphylococcus aureus* | | (2) *Salmonella enteritidis* | |
| Test 1 | Control mice | Phagocytosis ratio (%) | 37.3 ± 2.3 | (1) | 28.67 ± 0.29 | (1) |
| | | Phagocytized bacteria number I | 1.29 ± 0.14 | (1) | 0.48 ± 0.06 | (1) |
| | | Phagocytized bacteria number II | 3.55 ± 0.33 | (1) | 1.78 ± 0.13 | (1) |
| | Sample-treated mice | Phagocytosis ratio (%) | 55.73 ± 4.25 | (1.49) | 40.5 ± 2.6 | (1.41) |
| | | Phagocytized bacteria number I | 2.79 ± 0.47 | (2.18) | 0.93 ± 0.18 | (1.94) |
| | | Phagocytized bacteria number II | 4.99 ± 0.57 | (1.41) | 2.37 ± 0.32 | (1.33) |
| Test 2 | Control mice | Phagocytosis ratio (%) | 24.8 ± 2.1 | (1) | 16.0 ± 1.5 | (1) |
| | | Phagocytized bacteria number I | 0.59 ± 0.04 | (1) | 0.25 ± 0.06 | (1) |
| | | Phagocytized bacteria number II | 2.39 ± 0.19 | (1) | 1.31 ± 0.07 | (1) |
| | Sample-treated mice | Phagocytosis ratio (%) | 33.1 ± 8.9 | (1.34) | 18.5 ± 1.5 | (1.16) |
| | | Phagocytized bacteria number I | 0.91 ± 0.36 | (1.54) | 0.36 ± 0.02 | (1.44) |
| | | Phagocytized bacteria number II | 2.59 ± 0.39 | (1.08) | 1.37 ± 0.06 | (1.05) |
| Test 3 | Control mice | Phagocytosis ratio (%) | 26.83 ± 2.57 | (1) | 28.67 ± 0.29 | (1) |
| | | Phagocytized bacteria number I | 0.76 ± 0.11 | (1) | 1.78 ± 0.13 | (1) |
| | Sample-treated mice | Phagocytosis ratio (%) | 42.63 ± 3.36 | (1.59) | 35.50 ± 3.10 | (1.24) |
| | | Phagocytized bacteria number I | 1.37 ± 0.35 | (1.80) | 0.68 ± 0.06 | (1.42) |
| | | Phagocytized bacteria number II | 3.09 ± 0.51 | (1.02) | 1.97 ± 0.10 | (1.11) |

Note
1. In Table 1, each value indicates mean value ± standard deviation value.
2. Each parentheisized value is the activation index.
3. In Test 1, the extract prepared in Example 12 given herinafter was subcutaneously injected on the back of a mouse at a rate of 32 μg/0.1 ml(PBS)/mouse, and one group consisted of 10 mice.
4. In Test 2, the extract prepared in Example 25 given hereinafter was subcutaneously injected on the back of a mouse at a rate of 48 μg/0.1 ml(PBS)/mouse, and one group consisted of 10 mice.
5. In Test 3, the extract prepared in Example 36 given hereinafter was subcutaneously injected on the back of a mouse at a rate of 40.5 μg/0.1 ml(PBS)/mouse, and one group consisted of 10 mice.

(3) Reticuloendothelial Function Test:

The sample was treated into the intraperitoneal injection 7-weeks-old male mice of the ICR/JCL strain (having a body weight of 30±2 g) everyday during a period of 5 days.

In order to examine influences on the phagocytosis in the reticuloendothelial system, colloidal carbon (Pelikan acting carbon $C_{11}/1431a$ supplied by Günther Wag-

| | | | |
|---|---|---|---|
| | Sample-treated mice | 0.0224 ± 0.0096 | 16.281 ± 7.762 |
| Test 2 | Control mice | 0.0163 ± 0.0081 | 23.505 ± 13.595 |
| | Sample-treated mice | 0.0219 ± 0.0104 | 15.948 ± 5.430 |
| Test 3 | Control mice | 0.0063 ± 0.0009 | 48.550 ± 6.899 |
| | Sample-treated mice | 0.0115 ± 0.0020 | 27.120 ± 5.111 |
| Test 4 | Control mice | 0.0165 ± 0.0064 | 21.377 ± 10.619 |

TABLE 2-continued

| Results of Reticuloendothelial Function Test | | |
|---|---|---|
| | $K_2^{20}$ | $T \frac{1}{2}$ (min.) |
| Sample-treated mice | $0.0223 \pm 0.0095$ | $15.834 \pm 5.969$ |

Note
1. In Table 2, each value indicates mean value ± standard deviation value.
2. In Test 1, one group consisted of 12 mice, and the extract obtained in Example 12 given hereinafter was treated at a rate of 65 μg/0.1 ml(PBS)/mouse/day.
3. In Test 2, one group consisted of 12 mice, and the extract prepared in Example 25 given herinafter was treated at a rate of 97 μg/0.1 ml(PBS)/mouse/day.
4. In test 3, one group consisted of 6 mice, and the extract prepared in Example 26 given hereinafter was treated at a rate of 132 μg/0.1 ml(PBS)/mouse/day.
5. In Test 4, one group consisted of 22 mice, and the extract prepared in Example 36 given hereinafter was treated at a rate of 82 μg/0.1 ml(PBS)/mouse/day.

In each of the Tests 1 through 4, the phagocytic index was increased by treatment of the extract of the present invention and the half-value period in blood was shortened. Thus, it has been confirmed that the activity of catching colloidal carbon in the reticuloendothelial system is enhanced by treatment of the extract of the present invention.

Macrophages are divided into free type and fixed type, and free type cells are present in the bone marrow, blood, peritoneal cavity and alveolus and fixed type cells are present mainly in the spleen, lymph node and liver. The phagocytic activity test (1) on *Staphylococcus aureus* and the phagocytic activity test (2) on *Salmonella enteritidis* are tests made on the free type cells, and the reticuloendothelial test (3) is a test made on the fixed type cells. From the foregoing test results, it has been confirmed that the numbers of bacteria and foreign matters to be phagocytized by both the free type macrophages and the fixed type macrophages are increased by treatment of the extract of the present invention.

(2) Cytotoxicity Test:

(a) As the experimental animal, 7- to 10-weeks-old female mice of the BALB/c strain having a body weight of $22 \pm 2$ g were used. On the day when the sample was treated, BC-47 cells (the strain derived from the bladder cancer rat of the ACI strain and cultured in generations in a test tube) were applied to the intraperitoneal injection at a rate of $1 \times 10^7$ cells per mouse in both the treated group and the control group (treated with 0.1 ml of PBS) to effect immunization. After 7 days from the immunization, the peritoneal cavity of each mouse of the above two groups and the mormal mouse group was washed with RPMI-1640 medium to collect PEC. The collected cells were pooled respectively, and the PEC were washed 2 times with RPMI-1640 medium, centrifugally washed 1 time with 20% FBS-RPMI-1640 medium and then suspended in the latter-mentioned medium. With respect to each group, the PEC concentration was adjusted to $3.2 \times 10^5$ cells per ml by cell number counting using trypan blue.

(b) BC-47 cells cultured in a test tube were suspended in 20% FBS-RPMI-1640 medium to form a living cell suspension having a concentration of $8 \times 10^4$ living cells per ml.

(c) In a horizontal bottom type microplate for culturing of cells [Model N-1480 having 96 holes (wells), supplied by NUNC Co., Ltd., Sweden], 0.1 ml per hole of the PEC suspension ($3.2 \times 10^4$ cells) and 0.1 ml per hole of the test tube-cultured BC-47 cell suspension ($8 \times 10^3$ cells) were subjected to culturing at 37° C. for 24 hours in a 5% $CO_2$ incubator, and then, 0.05 μCi of $^{14}C$ thymidine was added to each hole and culturing was conducted under the same conditions for 24 hours.

(d) After completion of culturing, each hole was washed with PBS and BC-47 cells adhering and growing on the bottom face of the hole were collected on a filter paper by a cell harvester of the mini-mush type (supplied by Dynaetech Co., Ltd., England). The quantity of $^{14}C$ caught in the BC-47 cells in each hole (the number of $^{14}C$ atoms destroyed per minute, dpm) was measured by a liquid scintillation counter (Model LSC-673 supplied by Aloka Co., Ltd., Japan).

The propagation inhibition ratio was calculated according to the following formula:

$$\frac{A - B}{A} \times 100 \, (\%)$$

wherein A indicates the quantity ($\overline{M}$) (dpm/hole) of $^{14}C$ caught in BC-47 cells cultured singly and B denotes the quantity ($\overline{M}$) (dpm/hole) of $^{14}C$ caught in BC-47 cells cultured together with PEC of the normal mouse, the immunized mouse or the immunized and sample-treated mouse.

The activation index was calculated according to the following formula:

$$(C/D)$$

wherein C designates the propagation inhibition ratio ($\overline{M}$) of the immunized and sample-treated mouse and D stands for the propagation inhibition ratio ($\overline{M}$) of the immunized mouse (the sample was not treated).

The obtained results are shown in Table 3.

TABLE 3

| | | Enhanced Action of Cellular Immunity | | |
|---|---|---|---|---|
| | | Caught quantity of $^{14}C$ (dmp) | Propagation inhibition ratio (%) | Activation index |
| Test 1 | BC-47 cells cultured singly | $30884.3 \pm 349.7$ | 0 | — |
| | Normal mice | $27365.3 \pm 926.3$ | 11.39 | — |
| | Immunized mice | $22284.3 \pm 939.1$ | 27.85 | 1 |
| | Immunized and sample-treated mice | $16862.8 \pm 725.8$ | 45.40 | 1.63 |
| Test 2 | BC-47 cells cultured singly | $11208.2 \pm 411.1$ | 0 | — |
| | Normal mice | $9905.4 \pm 429.6$ | 11.62 | — |
| | Immunized mice | $6081.6 \pm 819.0$ | 45.74 | 1.00 |
| | Immunized and sample-treated mice | $2920.3 \pm 176.1$ | 73.95 | 1.62 |
| Test 3 | BC-47 cells cultured singly | $11208.2 \pm 411.1$ | 0 | — |
| | Normal mice | $9905.4 \pm 429.6$ | 11.62 | — |
| | Immunized mice | $6649.83 \pm 819.0$ | 40.67 | 1.00 |

TABLE 3-continued

| | Enhanced Action of Cellular Immunity | | |
|---|---|---|---|
| | Caught quantity of $^{14}C$ (dmp) | Propagation inhibition ratio (%) | Activation index |
| Immunized and sample-treated mice | 3960.2 ± 310.7 | 64.67 | 1.59 |

Note
1. In Test 1, the extract prepared in Example 12 given hereinafter was subcutaneously injected on the back of a mouse at a rate of 32 μg/0.1 ml(PBS)/mouse, and one group consisted of 10 mice.
2. In Test 2, the extract prepared in Example 25 given hereinafter was subcutaneously injected on the back of a mouse at a rate of 32 μg/0.1 ml(PBS)/mouse, and one group consisted of 10 mice.
3. In Test 3, the extract prepared in Example 36 given hereinafter was subcutaneously injected on the back of a mouse at a rate of 40.5 μg/0.1 ml(PBS)/mouse, and one group consisted of 10 mice.

From the foregoing results, it has been confirmed that by treatment of the extract of the present invention, propagation of BC-47 cells in mice can be inhibited and the cellular immunity to BC-47 cells can be enhanced.

(3) Acute Toxicity Test:

The acute toxicity was tested according to the Lichfield-Wilcoxon method (J. Pharm. Exp. Ther., 96, 99 (1949)) by using male mice of the ICR/JCL strain. It was found that the $LD_{50}$ value (mg/kg) of the extract prepared in Example 12 to 36 given hereinafter is 1990 to 2050. (intraperitoneal injection)

From the foregoing test results, it will readily be understood that the extract of the present invention is effectively used for preventing and inhibiting infectious diseases in patients having a reduced immunoactivity, for example, old patients or patients suffering from cancers while administered in combination with carcinostatic agents or for remedy of bacteria-infectious diseases while administered in combination with chemotherapeutic agents, or the extract of the present invention is administered to patients having reduced function of the liver for eliminating foreign substances (for example, medicines) so as to enhance the reduced function.

The extracts of the present invention may be administered to human body orally, by injection (intravenously, subcutaneously or intramuscularly) or in any other manner.

When the extracts of the present invention are employed in the form of solid preparations for oral administration, the preparations may be tablets, granules, powders, capsules or the like. The preparations may contain additives, for example, an excipient such as a saccharide or cellulose preparation, a binder such as starch paste or methyl cellulose, a filler, a disintegrator and so on, all being ones usually used in the manufacture of medical preparations. In case the extracts of the present invention are employed as oral liquid preparations, they may be of any form selected from aqueous preparations for internal use, suspensions, emulsions, syrups, etc., and further they may be in the form of dried porducts which are dissolved prior to the use.

When the extracts of the present invention are orally administered to adults, they may be employed in a dose of 3 to 20 mg/kg per day. Here, of course, the dose may be increased or decreased appropriately depending on the conditions of disease, the age of the patient, the form of the preparation administered, etc.

The extracts of the present invention may be injected in the form of aqueous solutions, suspensions or oily or aqueous emulsions, but usually the injections are prepared by dissolving or suspending them in aqueous liquid media such as sterile water of physiological saline solutions. If necessary, conventionally used dissolving agents, stabilizers, preservatives, additives for preparing isotonic solutions, etc. may be added to the injections.

The thus obtained injection preparations are administered intravenously, intramuscularly, subcutaneously or in any other appropriate manner. When the injections are administered to adults parenterally, they may contain 0.1 to 5 mg/kg per day. Of course, this dose level is increased or decreased appropriately depending on the conditions of disease, the age of the patient, the form of the preparation administered and the method of administration.

The present invention will now be described in detail with reference to the following Examples that by no means limit the scope of the present invention.

EXAMPLE 1

40 of 50% ethanol (V/V) was added to 5 kg of finely divided commercially available barrenwort (*Epimedium koreanum* Nak. of Korea growth), and heating extraction was carried out at 50° C. for 6 hours on a water bath by using a reflux condencer. After extraction, the mixture was filtered while the mixture was still warm and the residue was further extracted 3 times in the same manner as the above, each time using 20 l of fresh 50% ethanol (V/V). All the recovered filtrates were combined and then concentrated at 45° C. under reduced pressure to obtain 30 l of an aqueous extract. This extract was charged in a separating funnel and 20 l of ethyl acetate was added thereto, and the mixture was shaken sufficiently and only the aqueous layer was recovered. The aqueous layer was further extracted 3 times in the same manner as the above, each time using 20 l of fresh ethyl acetate. The aqueous layer was concentrated under reduced pressure and the residual ethyl acetate was removed by distillation, and the residue was filtered to obtain 22.5 l of a defatted aqueous extract.

EXAMPLE 2

20 l of water was added to 2 kg of finely divided commercially avilable barrenwort (*Epimedium koreanum*, Nak. of Korea growth), and heating extraction was carried out at 50° C. for 6 hours on a water bath by using a reflux condencer. After extraction, the mixture was filtered while the mixture was still warm, and the residue was further extracted 3 times in the same manner as the above, each time using 10 l of water. All the filtrates were combined and then concentrated at 45° C. under reduced pressure to obtain 12 l of an aqueous extract.

Then, 9.0 l of a defatted aqueous extract was obtained from the so obtained aqueous extract in the same manner as described in Example 1.

EXAMPLE 3

20 l of 50% Ethanol (V/V) was added to 2 kg of finely divided commercially available barrenwort (*Epimedium marcranthum* M. et. D, var. violaceum Fr.

of Japan growth), and the mixture was allowed to stand still at room temperature overnight. Then, the mixture was filtered and the residue was further extracted 3 times in the same manner as the above, each time using 10 l of fresh 50% ethanol (V/V). All the filtrates were combined and then concentrated at 45° C. under reduced pressure to obtain 12 l of an aqueous extract.

Then, 9.0 l of a defatted aqueous extract was obtained from the so obtained aqueous extract in the same manner as described in Example 1.

EXAMPLE 4

20 l of water was added to 2 kg of finely divided commercially available barrenwort (*Epimedium macranthum*, M. et. D, var. violaceum Fr. of Japan growth), and the mixture was allowed to stand still at room temperature overnight and was filtered and the residue was further extracted 3 times in the same manner as the above, each time using 10 l of fresh water. All the filtrates were combined and then concentrated at 45° C. under reduced pressure to obtain 12 l of the aqueous extract.

Then, 9.0 l of a defatted aqueous extract was obtained from the so obtained aqueous extract in the same manner as described in Example 1.

EXAMPLE 5

16 l of ethyl acetate was added to 2 kg of finely divided commercially available barrenwort (*Epimedium sagittatum* Bak. of China Lüta growth), and heating extraction was carried out at 50° C. on a water bath for 6 hours by using a reflux condencer. After extraction, the mixture was filtered while the mixture was still warm and the residue was further extracted 2 times in the same manner as the above, each time using 16 l of fresh ethyl acetate. The residue left after removal of the ethyl acetate-soluble portion was air-dried, and 16 l of water was added thereto. The mixture was extracted at 50° C. for 6 hours on a water bath by using a reflux condencer. Then, the residue was further extracted and filtered 2 times in the same manner as the above, each time using 16 l of fresh water. The filtrates were combined, concentrated at 45° C. under reduced pressure and filtered to obtain 9.0 l of an aqueous extract.

EXAMPLES 6 THROUGH 11

In the same manner as described in Example 1, 2 kg of finely divided commercially available barrenwort (*Epimedium koreanum* Nak. of Korea growth) is treated except that the extracting solvent and defatting solvent were changed as indicated below. The obtained results are shown below.

| Example No. | Extracting Solvent | Defatting Solvent | Amount of Defatted Aqueous Extract (l) |
| --- | --- | --- | --- |
| 6 | 50% methanol (V/V) | ethyl acetate | 9.0 |
| 7 | 50% acetone (V/V) | ethyl acetate | 9.0 |
| 8 | 50% dioxane (V/V) | ethyl acetate | 9.0 |
| 9 | 50% ethanol (V/V) | chloroform | 9.0 |
| 10 | 50% ethanol (V/V) | diethyl ether | 9.0 |
| 11 | 50% ethanol (V/V) | n-hexane | 9.0 |

EXAMPLE 12

13.5 l of ethanol was added to 4.5 l of the defatted aqueous extract obtained in Example 1, and the mixture was stirred and allowed to stand still overnight and the deposited precipitate was recovered by filtration. The precipitate was washed with 100 ml of ethanol and dissolved in 400 ml of water, and 1.6 l of ethanol was added to the solution and the deposited precipitate was recovered by filtration. The recovered precipitate was dried under reduced pressure to obtain 10 g of an intended extract. Then, the extract was extracted with 500 ml of water and filtered, and the filtrate was concentrated and dried under reduced pressure to obtain 8 g of a purified extract in the form of brown powder.

EXAMPLES 13 THROUGH 22

The extracts of the present invention and purified extracts of the present invention were obtained from 4.5 l each of the defatted aqueous extracts obtained in Examples 2 through 11 in the same manner as described in Example 12. The obtained results are shown below.

| Example No. | Employed, Defatted Aqueous Extract | Amount of Intended Extract (g) | Amount of Purified Extract (g) |
| --- | --- | --- | --- |
| 13 | aqueous extract obtained in Example 2 | 17.5 | 14.0 |
| 14 | aqueous extract obtained in Example 3 | 8.8 | 7.0 |
| 15 | aqueous extract obtained in Example 4 | 10.5 | 7.5 |
| 16 | aqueous extract obtained in Example 5 | 9.3 | 7.5 |
| 17 | aqueous extract obtained in Example 6 | 9.3 | 7.5 |
| 18 | aqueous extract obtained in Example 7 | 8.9 | 7.1 |
| 19 | aqueous extract obtained in Example 8 | 8.8 | 7.0 |
| 20 | aqueous extract obtained in Example 9 | 8.9 | 7.1 |
| 21 | aqueous extract obtained in Example 10 | 9.0 | 7.2 |
| 22 | aqueous extract obtained in Example 11 | 8.1 | 6.5 |

EXAMPLE 23

The defatted aqueous extract (4.5 l) obtained in Example 1 was treated in the same manner as described in Example 12 except that methanol was used as the precipitating solvent instead of ethanol, to obtain 4.6 g of an intended extract and 2.6 g of a purified extract.

EXAMPLE 24

The defatted aqueous extract (4.5 l) obtained in Example 1 was treated in the same manner as described in Example 12 except that acetone was used as the precipitating solvent instead of ethanol, to obtain 8.8 g of an intended extract and 6.4 g of a purified extract.

EXAMPLE 25

The defatted aqueous extract (4.5 l.) obtained in Example 1 was charged in a cellulose tube for dialysis (Visking tube supplied by Union Carbide Co., Ltd., U.S.A.) and dialysis was conducted in running water for 1 week. The internal liquid (the portion which included high-molecular compounds-containing fraction) was concentrated under reduced pressure to 500 ml. 2.0 l of ethanol was added to the concentrated liquid and the deposited precipitate was recovered by filtration. The recovered precipitate was dried under reduced pressure to obtain 12 g of an intended extract. Then, the extract was extracted with 500 ml of water and filtered, and the filtrate was concentrated and dried under reduced pressure to obtain 10 g of a purified extract in the form of brown powder.

EXAMPLES 26 THROUGH 33

In the same manner as described in Example 25, the defatted aqueous extracts (4.5 l each) obtained in Examples 2 through 11 were treated to obtain intended extracts and purified extracts of the present invention. The obtained results are shown below.

| Example No. | Employed, Defatted Aqueous Extract | Amount of Intended Extract (g) | Amount of Purified Extract (g) |
| --- | --- | --- | --- |
| 26 | aqueous extract obtained in Example 2 | 12.0 | 10.0 |
| 27 | aqueous extract obtained in Example 5 | 10.0 | 8.0 |
| 28 | aqueous extract obtained in Example 6 | 11.2 | 10.0 |
| 29 | aqueous extract obtained in Example 7 | 10.6 | 9.0 |
| 30 | aqueous extract obtained in Example 8 | 10.6 | 8.6 |
| 31 | aqueous extract obtained in Example 9 | 10.6 | 8.8 |
| 32 | aqueous extract obtained in Example 10 | 10.8 | 8.6 |
| 33 | aqueous extract obtained in Example 11 | 9.8 | 8.0 |

EXAMPLE 34

The defatted aqueous extract (4.5 l.) obtained in Example 3 was dialyzed by a PVA hollow fiber dialyzer including a polyvinyl alcohol hollow fiber membrane (Model KL-1-30 supplied by Kuraray Co., Ltd., Japan). 1.6 l. of ethanol was added to the so obtained, concentrated liquid (400 ml) and the deposited precipitate was recovered by filtration. The recovered precipitate was dried under reduced pressure to obtain 10.6 g of an intended extract. Then, the extract was extracted with 500 ml of of water and filtered, and the filtrate was concentrated and dried under reduced pressure to obtain 8.5 g of a purified extract.

EXAMPLE 35

In the same manner as described in Example 34, the deffatted aqueous extract obtained in Example 4 was treated to obtain 6.1 g of an intended extract, and 4.5 g of a purified extract.

EXAMPLE 36

The defatted aqueous extract (4.5 l) obtained in Example 1 was gradually mixed, with stirring, with ammonium sulfate until the saturation concentration of ammonium sulfate was reached, and the mixture was allowed to stand still overnight. The deposited precipitate was recovered by filtration, air-dried and extracted with 6 l. of water. The extract was charged in a cellulose tube for dialysis (Visking tube supplied by Union Carbide Co., Ltd., U.S.A.) and dialysis was conducted in running water for 6 days. The internal liquid (the portion which included high-molecular compounds-containing fraction) was concentrated under reduced pressure to 500 ml. 2.0 l of ethanol was added to the concentrated liquid and the deposited precipitate was recovered by filtration. The recovered filtrate was dried under reduced pressure to obtain 8.1 g of an intended extract. Then, the extract was extracted with 500 ml of water and filtered, and the filtrate was concentrated and dried under reduced pressure to obtain 6.0 g of a purified extract.

It was confirmed that the intended extracts obtained in Examples 12 through 36 have the foregoing characteristics.

What is claimed is:

1. A process to obtain an extract from barrenwort obtained from plants belonging to the genus Epimedium of the family of Berberidaceae, comprising the steps of
   (A) obtaining said barrenwort, and placing said barrenwort in an extraction solvent selected from the group consisting of
      (i) a mixture of water and a water-miscible organic solvent selected from the group consisting of lower alcohols, acetone, dioxane, and mixtures thereof,
      (ii) water,
      (iii) lower aliphatic acids having a concentration lower than one (1) normality,
      (iv) water-miscible lower amines at a concentration lower than one mole per liter, and
      (v) alkaline hydroxides easily soluble in water having a concentration lower than (1) one normality,
   (B) filtering the resulting solution of said barrenwort and said extraction solvent of step (A) to obtain a filtrate,
   (C) concentrating said filtrate of step (B) under reduced pressure to obtain an aqueous extract,
   (D) adding to said aqueous extract of step (C) an organic defatting solvent selected from the group consisting of
      (i) lower aliphatic esters,
      (ii) chloroform,
      (iii) diethyl ether,
   and
      (iv) n-hexane,
   (E) shaking the resulting mixture comprising said organic defatting solvent of step (D) and said aqueous extract of step (C), collecting the aqueous layer alone, and removing the small amount of said organic defatting solvent left in said aqueous layer,
   (F) filtering the resulting aqueous layer of step (E) to obtain a defatted aqueous extract,
   (G) adding to said defatted aqueous extract of step (F) a water-miscible, organic fractional precipitation solvent selected from the group consisting of lower alcohols, acetone, and mixtures thereof, thereby effecting a precipitation, wherein the volume of said water-miscible, organic fractional precipitation solvent is not smaller than the volume of said defatted aqueous extract,
   (H) recovering the precipitate resulting from step (G) by filtration,
   (I) washing said precipitate of step (H) with a water-miscible, organic washing solvent, selected from the group consisting of lower alcohols, acetone and mixtures thereof, wherein the volume of said washing solvent used is about 5 to about 50 times the weight of said washed precipitate,
   (J) mixing the resulting washed precipitate of step (I) with a volume of water from about 20 to about 50 times the weight of said washed precipitate,
   (K) adding to the solution resulting from step (J) a volume of water-miscible, organic, second fractional precipitation solvent selected from the group consisting of lower alcohols, acetone and mixtures thereof, that is three (3) or more times the volume of the solution resulting from step (J) to effect precipitation, (L) recovering the precipitate of step (K) by filtration and drying the same to obtain a dry precipitate, the resulting extract having the following characteristics:
(1) Properties:
   (a) Brown powder
   (b) Weakly acidic (pH of about 6.5 (when 100 mg of extract is dissolved in 50 ml of water)
(2) Solubility:
   (a) Soluble in water
   (b) Insoluble in methanol, ethanol, acetone, ethyl acetate, diethyl ether, hexane and chloroform
(3) Color Reactions:
Positive to
   (a) anthrone-sulfuric acid reaction,
   (b) Bial's reaction,
   (c) Molisch's reaction and
   (d) skatol reaction;
negative to
   (a) ninhydrin reaction,
   (b) 2,4-DNP reaction,
   (c) Seliwanoff's reaction and
   (d) naphthoresorcinol reaction
(4) Saccharides composition: arabinose and galactose
(5) Infrared absorption:
   $\nu_{max}^{KBr}(cm^{-1}) 3400, 1600, 1400, 1100$
(6) U.V. Absorption:
   $\lambda_{max}^{H2O}(nm) 280, 325$ 2. The process as defined by claim 1, wherein said barrenwort is divided, and said process further comprises the steps of:
(M) said dry precipitate of step (L) is mixed with a volume of water that is about 20 or more times the weight of said dry precipitate of step (L), stirring the resulting mixture, and filtering the mixture, and
(N) concentrating and drying the filtrate of step (M), the resulting extract having said characteristics (1)–(6).

3. A process to obtain an extract from barrenwort obtained from plants belonging to the genus Epimedium of the family of Berberidaceae, comprising the steps of
(A) obtaining said barrenwort, and placing said barrenwort in an extraction solvent selected from the group consisting of
   (i) a mixture of water and a water-miscible organic solvent selected from the group consisting of lower alcohols, acetone, dioxane, and mixtures thereof,
   (ii) water,
   (iii) lower aliphatic acids having a concentration lower than one (1) normality,
   (iv) water-miscible lower amines at a concentration lower than one mole per liter,
and
   (v) alkaline hydroxides easily soluble in water having a concentration lower than one (1) normality,
(B) filtering the resulting solution of said barrenwort and said extraction solvent of step (A) to obtain a filtrate,
(C) concentrating said filtrate of step (B) under reduced pressure to obtain an aqueous extract,
(D) adding to said aqueous exctact of step (C) an organic defatting solvent selected from the group consisting of
   (i) lower aliphatic esters,
   (ii) chloroform,
   (iii) diethyl ether,
and
   (iv) n-hexane,
(E) shaking the resulting mixture comprising said organic defatting solvent of step (D) and said aqueous extract of step (C), collecting the aqueous layer alone, and removing the small amount of said organic defatting solvent left in said aqueous layer,
(F) filtering the resulting aqueous layer of step (E) to obtain a defatted aqueous extract,
(G) charging said defatted aqueous extract in a semipermeable membrane cellulose tube for a dialysis, carrying out said dialysis using water as the external liquid, and collecting the internal liquid which includes the high molecular weight compounds,
(H) concentrating to about 1/10 said internal liquid obtained by step (G),
(I) adding to the concentrated liquid obtained by step (H) a volume of water-miscible, organic, precipitating solvent selected from the group consisting of lower alcohols, acetone and mixtures thereof, about three (3) or more times the volume of said concentrated liquid thereby forming a precipitate,
(J) recovering the precipitate of step (I) by filtration and drying the same to form a dry precipitate,
the resulting extract having the following characteristics (1)–(6);
(1) Properties:
   (a) Brown Powder
   (b) Weakly acidic (pH of about 6.5 when 100 mg of the extract is dissolved in 50 ml of water)
(2) Solubility:
   (a) Soluble in water
   (b) Insoluble in methanol, ethanol, acetone, ethyl acetate, diethyl ether, hexane and chloroform
(3) Color Reactions:
Positive to
   (a) anthrone-sulfuric acid reaction,
   (b) Bial's reaction,
   (c) Molisch's reaction and
   (d) skatol reaction;
negative to
   (a) ninhydrin reaction,
   (b) 2,4-DNP reaction,
   (c) Seliwanoff's reaction and
   (d) naphthoresorcinol reaction
(4) Saccharides composition: arabinose and galactose
(5) Infrared Absorption:
   $\nu_{max}^{KBr}(cm^{-1}) 3400, 1600, 1400, 1100$
(6) U.V. Absorption:
   $\lambda_{max}^{H2O}(nm) 280, 325$ 4. The process as defined by claim 3, wherein said barrenwort is divided, and said process further comprises the steps of:
(K) said dry precipitate of step (J) is mixed with a volume of water that is about 20 or more times the weight of said dry precipitate of step (J), stirring the resulting mixture, and filtering the mixture, and
(L) concentrating and drying the filtrate of step (K), the resulting extract having said characteristics (1)–(6).

5. The process as defined by claim 1, 2, 3, wherein said plants are selected from the group consisting of *Epimedium koreanum* Nakai, *Epimedium marcranthum*, M. et D. var. violaceum Fr. and *Epimedium sagittatum* Bak.

6. The product obtained by the process defined by claim 1.

7. The product obtained by the process defined by claim 2.

8. The product obtained by the process defined by claim 3.

9. The product obtained by the process defined by claim 4.

* * * * *